United States Patent [19]

Aoki et al.

[11] 4,094,592

[45] June 13, 1978

[54] OPHTHALMIC EXAMINATION CHART PROJECTOR

[75] Inventors: Mitsugu Aoki, Tokyo; Taketoshi Ishihara, Soka, both of Japan

[73] Assignee: Tokyo Kogaku Kikai Kabushiki Kaisha, Tokyo, Japan

[21] Appl. No.: 762,338

[22] Filed: Jan. 25, 1977

[30] Foreign Application Priority Data

Feb. 3, 1976 Japan ............................. 51-11220[U]

[51] Int. Cl.² ............................................. A61B 3/02
[52] U.S. Cl. ........................................ 351/30; 351/34
[58] Field of Search ...................... 351/30, 32, 33, 34, 351/35, 36, 37; 353/42, 21, 110, 116

[56] References Cited

U.S. PATENT DOCUMENTS

| | | | |
|---|---|---|---|
| 2,570,652 | 10/1951 | Dilks | 353/110 |
| 3,655,276 | 4/1972 | Wilkinson | 351/30 |
| 3,711,195 | 1/1973 | Gehlert | 353/116 |

Primary Examiner—Paul A. Sacher
Assistant Examiner—Rodney Bovernick
Attorney, Agent, or Firm—Stevens, Davis, Miller & Mosher

[57] ABSTRACT

Ophthalmic examination chart projector including a rotatable chart carrying disc and a mask plate which are co-axial with each other. A light source and a projecting lens assembly are provided for projecting one of the charts on the disc and one of the mask openings onto a screen. An index tube is rotatably mounted in the projecting optical path and carrying a colored filter on the inner periphery thereof. Thus, an astigmatic index can be projected on the peripheral portion of the astigmatic examination chart. The chart carrying disc, the mask plate and the astigmatic index tube can be controlled by knobs all provided on the front panel of the projector.

6 Claims, 4 Drawing Figures

OPHTHALMIC EXAMINATION CHART PROJECTOR

The present invention relates to ophthalmic examination chart projectors adapted for projecting charts which are to be used for testing visual acuities of patients.

In testing visual acuities, it has been known to employ a chart projector for projecting an examination chart on a screen. Such a chart projector has conventionally been used in combination with a ophthalmoscopic instrument which includes a plurality of trial lenses. It has been experienced, however, that conventional chart projectors have been inconvenient when they are used in combination with such ophthalmoscopic instruments because operators normally stand by the ophthalmoscopic instruments for operation thereof and must move to the chart projectors for switching charts to be projected from one to another. In order to eliminate the inconvenience, it has been proposed to drive the chart projectors through remote control means, such as electrically operated means. However, such a proposal is disadvantageous because there must be provided complicated and expensive drive mechanisms.

Another inconvenience experienced in conventional chart projectors relates to indexing in astigmatic examination. It has been a conventional practice that an operator stands aside a screen where an examination chart is projected and directly indicate a specific part thereon by using a stick or the like. However, since the projecting screen is located at a distance from the projectors, the examiner has to frequently move between the projector and the screen.

The present invention has therefore an object to provide chart projectors in which the aforementioned problems are eliminated.

Another object of the present invention is to provide chart projectors in which all operating members are located in the front panel thereof.

A further object of the present invention is to provide chart projectors having means for indexing the astigmatic examination chart.

Still further object of the present invention is to provide chart projectors in which chart carrying discs are mounted so that they can readily be removed.

According to the present invention, in order to accomplish the above and other objects, there is provided an ophthalmic examination chart projector comprising a circular chart carrying disc having a plurality of ophthalmic examination charts disposed along a pheripheral portion of the disc, a circular mask plate having a plurality of openings which are peripherally spaced apart from each other, means for supporting said chart carrying disc and the mask plate co-axially and rotatably about a horizontal axis, illumination light source means provided at one side of the chart carrying disc and the mask plate, projection lens means provided at the other side of the chart carrying disc and the mask plate so as to define together with the light source means a projecting optical path which pass through the peripheral portion of the disc, one of said chart carrying disc and said mask plate being in engagement with a first operating member extending co-axially from said one of the chart carrying disc and the mask plate so that it is rotated by the first operating member, the other of the chart carrying disc and the mask plate being in engagement with a second operating member which is located outside the periphery of said other of the disc and the plate and extending in parallel with and in the same direction as the first operating member, whereby one of the charts on the disc and one of the openings in the mask plate can be positioned in the optical path through actuation of the first and the second operating members. Since the first and second operating members extend in the same direction, it is possible to actuate these members at the same side of the projector. It is preferable to arrange these operating members so that they can be actuated at the front side, that is, the side of the projector where the projection lens means is located.

In a preferable aspect of the present invention, the projector includes an astigmatic index projecting means for projecting an astigmatic index on the peripheral portion of the projected chart. More preferably, the examination charts include an astigmatic chart having a peripheral portion diametrically wider than those in the other charts, means being provided for projecting an index to the peripheral portion of the astigmatic chart and for moving the index circumferentially of the chart as desired. The index may be in the form of a colored filter or of any other suitable means. According to a further preferable aspect of the present invention, the chart carrying disc is readily removably mounted on the projector.

The above and other objects and the features of the present invention will become apparent from the following descriptions of a preferred embodiment taking reference to the accompanying drawings, in which.

Figure 1:
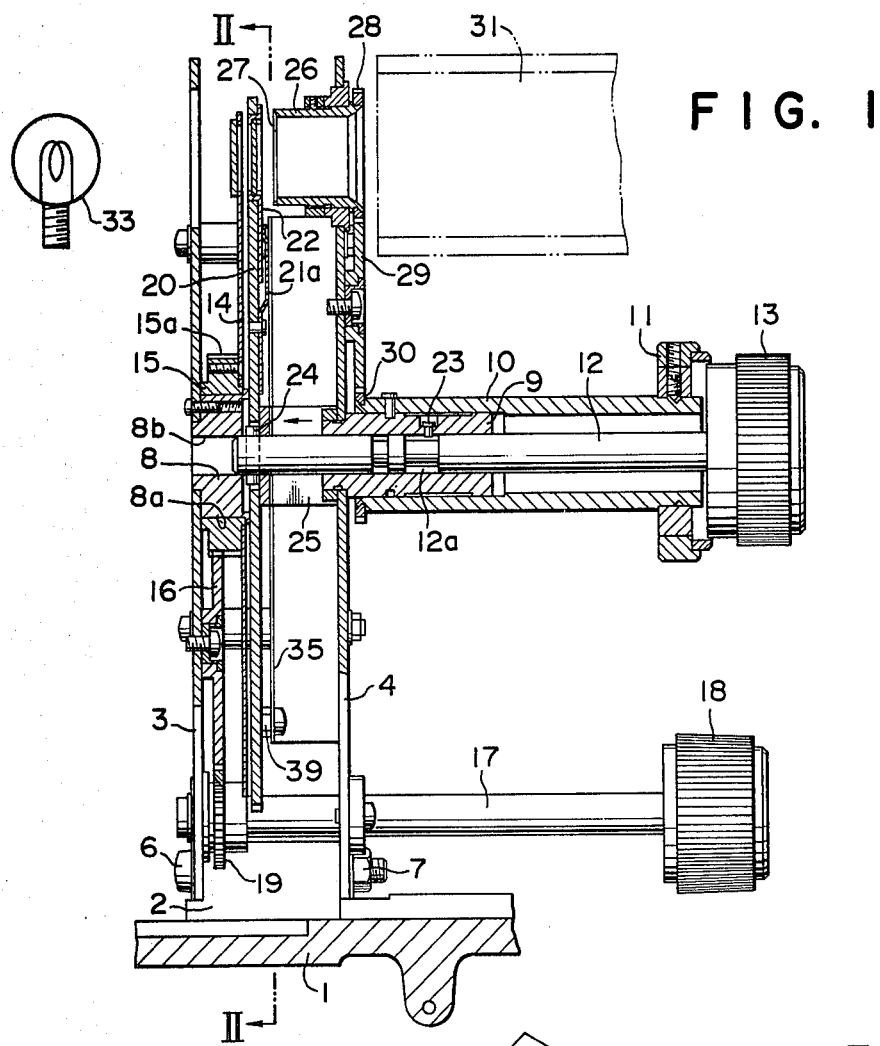
FIG. 1 is a sectional side view of a chart projector in accordance with one embodiment of the present invention.

Referring to the drawings, the chart projector shown therein includes a base 1 which has a pair of brackets 2 formed at the opposite sides thereof although only one of them can be seen in FIG. 1. A pair of support plates 3 and 4 are secured to the brackets 2 by means of bolts 6 and nuts 7 and spaced apart from each other. The plate 3 carries a cylindrical block 8 which is secured to the central portion of the plate 3 and has a cylindrical outer surface 8a and an axial bore 8b.

Coaxially with the block 8, the plate 4 carries a sleeve 9 which is rotatable about its own axis and has a hollow operating shaft 10 secured thereto. At the free end, that is, the front end of the shaft 10, there is provided an operating knob 11. A further shaft 12 is disposed in the sleeve 9 for rotation and axial movement. The shaft 12 has a front end projecting beyond the front end of the shaft 10 and an operating knob 13 is secured to the front end of the shaft 12.

A mask plate 14 is rotatably mounted on the block 8 by means of a boss 15 which is provided on the mask plate 14 and rotatably engages the cylindrical surface 8a of the supporting block 8. The boss 15 has an outer surface formed with external gear teeth 15a which are in meshing engagement with a gear 16 rotatably supported on the plate 3.

Figure 2:
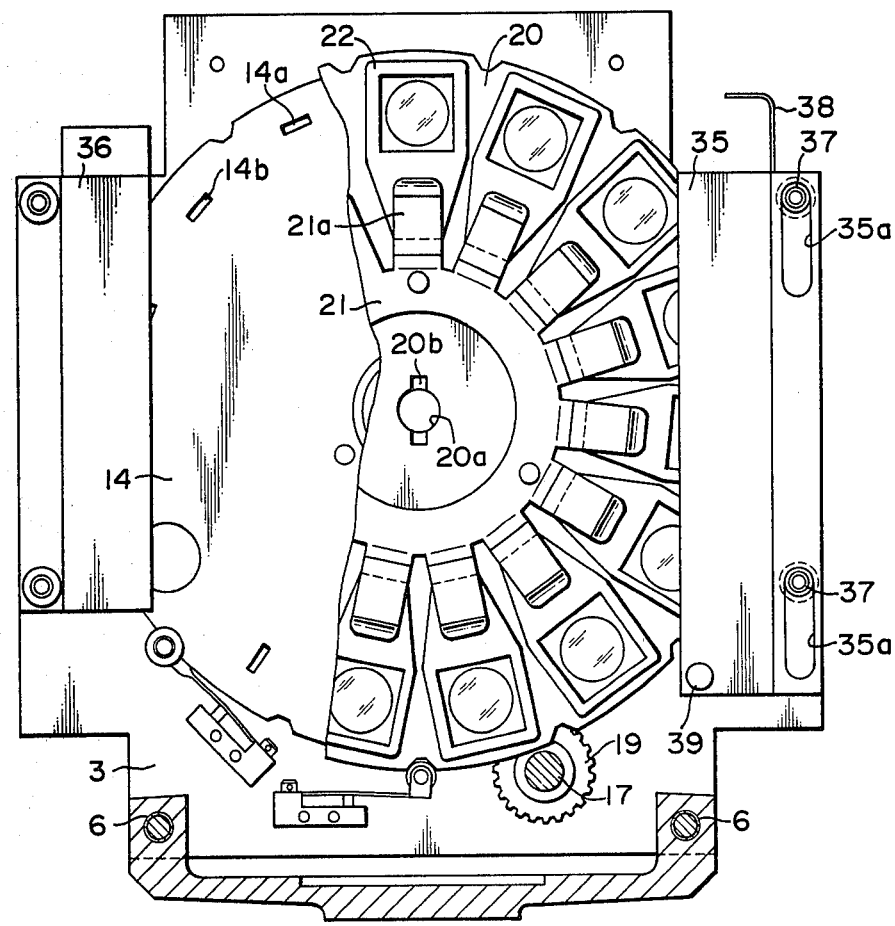
FIG. 2 is a view substantially along the line II—II in FIG. 1 with parts cut away to show details clearly.

On the plates 3 and 4, there is also rotatably supported a mask plate operating shaft 17 which extends forwardly and has an operating knob 18 secured to the front end thereof. The shaft 17 carries a gear 19 which engages the gear 16. As shown in FIG. 2, the mask plate 14 is formed with a plurality of openings, such as the openings 14a and 14b which are arranged along the periphery of the plate 14. Thus, the mask plate 14 can be rotated by the shaft 17 to place one of the openings in operative or projecting position.

A chart carrying disc 20 is disposed at the front side of the mask plate 14. The disc 20 has a spring member 21 which is formed with a plurality of circumferentially spaced radially outwardly extending spring leaves 21a for holding charts 22 on the disc 20. The disc 20 is formed at its center portion with an axial hole 20a and a diametrically outwardly extending slot 20b.

Figure 3:
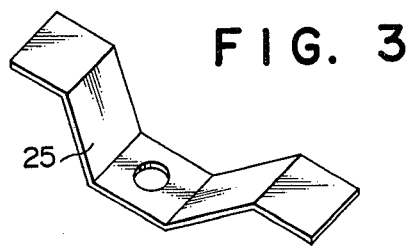
FIG. 3 is a perspective view of a spring used in the chart projector.

The shaft 12 passing through the sleeve 9 has an annular recess 12a at the intermediate portion and a pin 23 provided on the sleeve 9 engages with the recess 12a, whereby the shaft 12 is rotable and axially slidable within the extent of the axial length of the recess 12a with respect to the sleeve 9 and the shaft 10. The shaft 12 has a pin 24 which passes diametrically through the shaft 12 and extends beyond the outer surface of the shaft 12. A leaf spring 25 having a configuration as shown in FIG. 3 is disposed between the plate 4 and the pin 24 on the shaft 12 to force the shaft 12 toward the disc 20 so that the rear end of the shaft 12 engages the axial bore 20a in the disc 20 and the pin 24 with the slot 20b. Thus, the shaft 12 is brought into driving engagement with the disc 20.

On the upper portion of the plate 4, there is rotatably mounted an index tube 26 which has a colored filter 27 disposed at a portion of the inner periphery thereof. The tube 26 is formed at the front outer periphery with gear teeth 28 which are in meshing engagement with an intermediate gear 29 which is in turn in engagement with a gear 30 secured to the rear end of the shaft 10. Thus, the tube 26 can be rotated as desired by the shaft 10 through the gears 30, 29 and 28.

Axially forwardly of the index tube 26, there is arranged a projecting lens assembly 31 and an illuminating light source 33 is disposed at the rear side of the plate 3. A projecting optical path is thus defined by the light source 33 and the lens assembly 31, and the index tube 26 is located in this optical path. The optical path is so located that one of the charts 22 on the disc 20 and one of the openings in the mask plate 14 are appropriately brought into the path by rotating the disc 20 and the plate 14 through the shafts 17 and 12 for projecting them through the lens 31.

Figure 4:
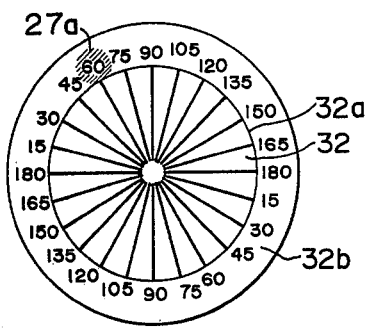
FIG. 4 is a front view of an astigmatic examination chart.

According to the illustrated embodiment, the index on the tube 26 is formed by the colored filter 27 which is located outside the confine of transparent or chart area of any normal chart except the astigmatic examination chart. In case of the latter chart, there is further an annular transparent area 32b outside the confine 32a defining a chart area 32 and the index 27 is projected on this annular area 32b as shown by a shadow area 27a in FIG. 4. It will be understood that the position of the projected index 27a can be moved as desired by rotating the tube 26 by the shaft 10. It will further be understood that the index 27 is not projected when any chart other than the astigmatic chart is being projected.

The plate 4 is provided at the side facing the disc 20 with a pair of disc guide members 35 and 36 vertical grooves in which the opposite sides of the disc 20 are respectively inserted. In mounting the chart carrying disc 20, the shaft 12 is axially shifted toward right as seen in FIG. 1 against the action of the spring 25, then the disc 20 is inserted along the guide members 35 and 36 and thereafter the shaft 12 is released to allow it to return under the influence of the spring 15 until the rear end of the shaft 12 engages the central hole 20a in the disc 20.

As shown in FIG. 2, the guide member 35 has a pair of vertically extending slots 35a which engage a pair of pins 37 provided on the plate 4, whereby the guide member 35 is vertically movable within a limited extent. The guide member 35 is provided at the upper end with an L-shaped hook 38 so that the guide member 35 can readily be lifted by means of the hook 38. At the lower end portion of the guide member 35, there is provided a pin 39 extending in the direction of the disc 20. The pin 39 is normally located below the adjacent edge of the disc 20, however, when the guide member 35 is moved upwards as described above, the pin 39 comes into engagement with the edge of the disc 20 so as to force the latter upwardly. Thus, the chart carrying disc 20 can be readily removed from the projector simply by pulling the shaft 12 forwardly to disengage the rear end thereof from the disc 20 and moving the guide member 35 upwardly until the disc 20 is lifted by the pin 39. Then, the disc 20 can be easily gripped by fingers and taken out of the projector.

The illustrated embodiment of the present invention is advantageous in that the chart carrying disc 20, the mask plate 14 and the index tube 26 can be actuated by the knobs all located on the front panel of the projector. Therefore, the operator can handle the projector at the same position where the ophthalmoscopic instrument is handled. Further, the astigmatic index can easily be controlled and therefore the inconveniencies in the conventional chart projectors can be eliminated.

The invention has thus been shown and described with reference to a specific embodiment, however, it should be noted that the invention is in no way limited to the details of the illustrated structures but changes and modifications may be made without departing from the scope of the appended claims.

We claim:

1. Ophthalmic examination chart projector comprising a circular chart carrying disc having a plurality of ophthalmic examination charts disposed along a peripheral portion of the disc, a circular mask plate having a plurality of openings which are peripherally spaced apart from each other, means for supporting said chart carrying disc and the mask plate co-axially and rotatably about a horizontal axis, illumination light source means provided at one side of the chart carrying disc and the mask plate, projection lens means provided at the other side of the chart carrying disc and the mask plate so as to define together with the light source means a projecting optical path which pass through the peripheral portion of the disc, one of said chart carrying disc and said mask plate being in engagement with a first operating member extending co-axially from said one of the chart carrying disc and the mask plate so that it is rotated by the first operating member, the other of the chart carrying disc and the mask plate being in engagement with a second operating member which is located outside the periphery of said other of the disc and the plate and extending in parallel with and in the same direction as the first operating member, whereby one of the charts on the disc and one of the openings in the mask plate can be positioned in the optical path through actuation of the first and the second operating members, said projector further including astigmatic index means comprising a rotatable member positioned in said optical path and having an index, and a third operating member extending in the same direction as the first and second operating members and in engagement with said rotatable member for rotating it to circumferentially move said index.

2. Chart projector in accordance with claim 1 in which said third operating member is a hollow shaft through which said first operating member is axially passed.

3. Chart projector in accordance with claim 1 in which said index is a coloured filter.

4. Chart projector in accordance with claim 1 in which said index is so located that it is projected outside confine of any chart and the charts include an astigmatic examination chart which has an annular transparent area outside the confine of chart area, the index being located so as to be projected in the transparent area.

5. Chart projector in accordance with claim 4 in which said astigmatic examination chart has an angular index in the transparent area.

6. Chart projector in accordance with claim 1 in which said chart carrying disc is mounted removably on the projector and guide means is provided for guiding the disc when it is inserted in position, said guide means being movable at least within a limited extent and having means engageable with said disc when it is moved so as to force the disc out of the projector.

* * * * *